US00PP35805P2

(12) United States Plant Patent
Bergman

(10) Patent No.: US PP35,805 P2
(45) Date of Patent: May 14, 2024

(54) ***MANDEVILLA* PLANT NAMED 'MANZ0031'**

(50) Latin Name: ***Mandevilla sanderi* (Hemsl.) Woodson**
Varietal Denomination: MANZ0031

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/212,271

(22) Filed: Jun. 21, 2023

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — Dale Skalla

(57) ABSTRACT

A new *Mandevilla* plant named 'MANZ0031' particularly distinguished by its large deep red flowers, glossy and smooth dark green foliage, compact and bushy plant habit with excellent branching and flower production and fast flowering response.

1 Drawing Sheet

Latin name of the genus and species of the plant claimed: *Mandevilla sanderi* (Hemsl.) Woodson.

Varietal denomination: 'MANZ0031'.

BACKGROUND OF THE NEW PLANT

The present invention comprises a new *Mandevilla*, botanically known as *Mandevilla sanderi*, and hereinafter referred to by the variety name 'MANZ0031'.

'MANZ0031' is a product of a planned breeding program. The new cultivar has deep red flower color, glossy and smooth dark green foliage, compact and bushy plant habit with excellent branching and flower production and fast flowering response.

'MANZ0031' originates from a hybridization made in a controlled breeding program in Amatitlan, Guatemala. The pollinations were made in 2014.

The female parent was an unpatented, proprietary plant identified as 'DIP-195' and having larger sized deep red flowers, a more vigorous growth habit and one week slower flowering response than 'MANZ0031'.

The male parent of 'MANZ0031' was an unpatented, proprietary plant identified as 'DIP-059', having smaller red flowers, a more compact growth habit, less flower production and smaller foliage than 'MANZ0031'.

The resulting seeds were sown in February 2015 and 'MANZ0031' was selected as one flowering plant within the progeny of the stated cross in December 2015 in a greenhouse in Gilroy, California.

The first act of asexual reproduction of 'MANZ0031' was accomplished when vegetative stem cuttings were propagated from the initial selection in March 2016 in a controlled environment in Gilroy, California.

BRIEF SUMMARY OF INVENTION

Horticultural examination of plants grown from cuttings of the plant initiated in March 2016 in Gilroy, California, and continuing thereafter, has demonstrated that the combination of characteristics as herein disclosed for 'MANZ0031' are firmly fixed and are retained through successive generations of asexual reproduction.

'MANZ0031' has not been observed under all possible environmental conditions. The phenotype may vary significantly with variations in environment such as temperature, light intensity and day length.

A Plant Breeder's Right for this cultivar has not yet been applied for. 'MANZ0031' has not been made publicly available prior to the effective filing date of this application, notwithstanding any disclosure that may have been made less than one year prior to the effective filing date of this application by the inventor or another who obtained 'MANZ0031' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

The accompanying photographic drawings show typical flower and foliage characteristics of 'MANZ0031' with colors being as true as possible with an illustration of this type.

Figure 1:
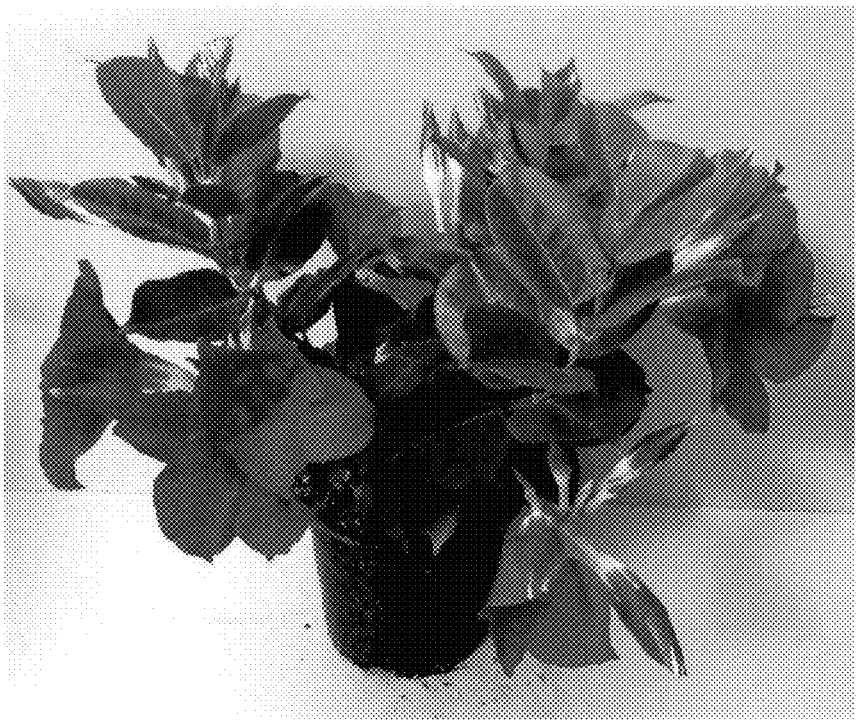
Figure 2:
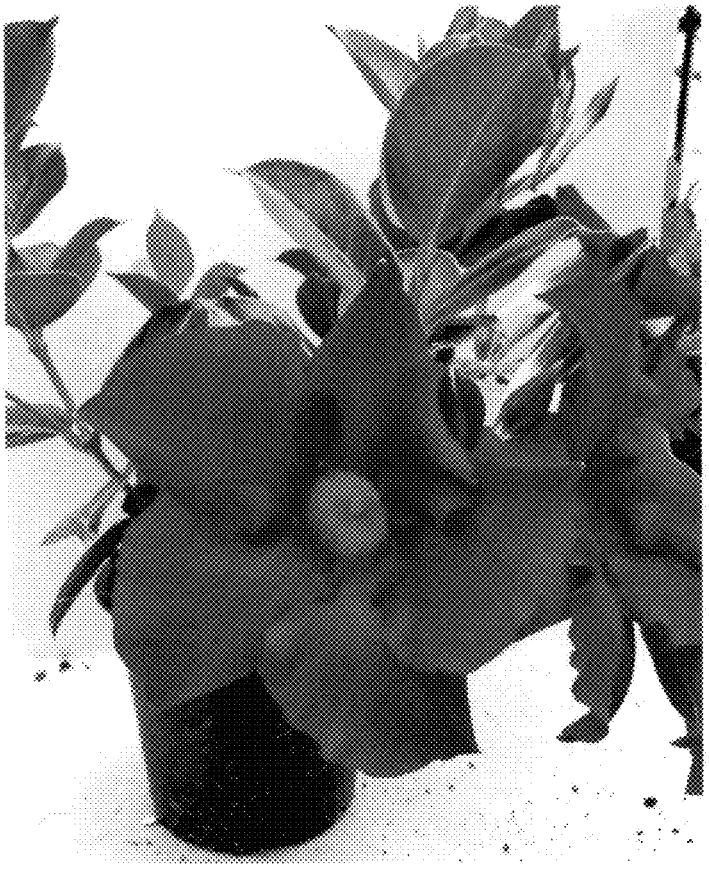

The photographic drawings show in FIG. 1, a six month old flowering potted plant of the new variety taken Andijk, The Netherlands in May 2023 and in FIG. 2, a close-up of a flower on the same six month old plant taken in Andijk, The Netherlands in May 2023.

DETAILED BOTANICAL DESCRIPTION

The detailed botanical description was completed in May 2023 in Gilroy, California. The plants were growing in quart size pots in a greenhouse; they were about 5 months in age.

In the following description, color references are made to The Royal Horticultural Society Colour Chart, 2015 edition.

TABLE 1

DIFFERENCES BETWEEN THE NEW VARIETY 'MANZ0031' AND A SIMILAR VARIETY

| | 'MANZ0031' | Rio Deep Red 'FISRIX DERED' U.S. Plant Pat. No. 20,714 |
|---|---|---|
| Flower size: | 10% larger | Smaller |
| Foliage size: | 10% smaller | Larger |
| Leaf petiole adaxial side: | Green | Reddish with anthocyanin |
| Leaf petiole length: | 0.7-1.2 cm | 1.5-2.0 cm |

Plant:

*Form, growth, and habit.*—Perennial or sub-shrub, herbaceous younger stems, woody at base of older stems, semi-upright, with slight tendency of developing vines depending on season and light intensity. Time for producing a commercial, flowering plant approximately is 18-20 weeks for one plant in a quart size container.

*Plant height.*—23 cm.

*Plant height (inflorescence included).*—23 cm.

*Plant width.*—29 cm.

Roots:

*Number of days to initiate roots.*—About 20-23 days at about 22 degrees C.

*Number of days to produce a rooted cutting plant.*—5 weeks at about 22 degrees C.

*Type.*—Fibrous, a little fleshy, free branching.

*Color.*—RHS 155D.

Foliage:

*Arrangement of leaves.*—Simple leaf, opposite and decussate.

*Immature leaf, color upper surface.*—RHS 137C.

*Immature leaf, color lower surface.*—RHS 138B.

*Mature leaf, color upper surface.*—Between RHS 137A and RHS 139A.

*Mature leaf, color lower surface.*—RHS 138A.

*Length.*—6.3-7.1 cm.

*Width.*—3.5-4.0 cm.

*Shape.*—Ovate.

*Base shape.*—Rounded.

*Apex shape.*—Broadly acuminate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 139D.

*Color of vein (midrib), lower surface.*—RHS 139D.

*Bulging between veins.*—Absent to weak.

*Petiole color.*—RHS 138B.

*Length.*—0.7-1.2 cm.

*Diameter.*—0.2 cm.

*Petiole, texture.*—Glabrous.

Stem:

*Branching characteristics.*—Moderately free branching.

*Quantity of main branches per plant.*—4-5.

*Color of stem.*—RHS 146B.

*Length of stem.*—17-22 cm.

*Diameter (at about mid-point).*—0.25 cm.

*Length of internodes.*—1.3-3.0 cm.

*Stem, texture.*—Smooth and glabrous.

*Number of climbing tendrils.*—None present.

Inflorescence:

*Type of inflorescence.*—Raceme of several flowers, emerging from nodes of the stem.

*Number of flowers per inflorescence.*—7-13.

*Blooming habit.*—Continuously through the summer months.

*Quantity of flowers per plant.*—About 20 in various stages of development.

*Lastingness of individual blooms on the plant.*—Approximately 8-10 days, depending on temperature.

*Fragrance.*—Absent.

Peduncle:

*Color.*—Green, RHS 141A.

*Length.*—7.0-9.5 cm.

*Diameter.*—0.2 cm.

*Texture.*—Smooth, glabrous, somewhat glossy.

Bud (just before opening/showing color):

*Color.*—RHS 185A.

*Length.*—9.1 cm.

*Width.*—1.8 cm.

*Shape.*—Elongated, spindle shape.

Immature flower:

*Diameter.*—7.3 cm.

*Vertical diameter.*—About 7.0 cm.

*Color upper surface.*—RHS 146A with tones of RHS 185A and RHS 53A.

*Color lower surface.*—RHS 185AC.

Mature flower:

*Flower type.*—Single.

*Shape.*—Funnelform, funnel shaped base, formed by partly 5 fused petals, with the petal lobes opening outwards, and a little overlapping.

*Flower, horizontal diameter.*—8.2 cm.

*Flower, vertical diameter.*—About 7.3 cm.

*Flower, diameter of the funnel.*—1.4 cm.

*Flower color, general.*—Dark red.

*Flower color, upper surface.*—RHS 146A with tones of RHS 185A and RHS 53A.

*Flower color, lower surface.*—RHS 185A.

*Color of the funnel, inner side.*—RHS 168A.

*Color of the funnel, outside.*—RHS 53C with slightly darker and lighter tones.

*Petal, shape.*—Roughly ovate, moderately asymmetric.

*Petal apex shape.*—Acute to cuspidate.

*Petal base shape.*—Fused.

*Petal margin.*—mainly entire and mildly undulate.

*Petal length, from the corolla opening.*—3.5 cm.

*Petal width, maximum.*—3.3-3.5 cm.

*Corolla, texture of upper surface.*—Glabrous, papillose.

*Corolla, texture of lower surface.*—Glabrous, papillose.

*Corolla, diameter.*—8.2 cm.

*Corolla, lobe.*—Moderately asymmetric.

*Corolla throat length.*—6.3 cm.

*Corolla throat color, inner side.*—RHS 168A.

*Corolla throat color, outer side.*—RHS 53C with slightly darker and lighter tones of RHS 53B and RHS 53D.

*Pedicel, color.*—Light green, RHS 145A.

*Length.*—1.6-1.8 cm.

*Diameter.*—0.2 cm.
*Pedicel, texture.*—Smooth, glabrous.

Calyx:
*Form.*—5 sepals, closely attached to the base of the flower.
*Color, visible outer surface.*—RHS 145B.
*Length.*—0.9 cm.
*Width.*—0.4 cm.
*Shape.*—Subulate.
*Apex shape.*—Acute.
*Based.*—Fused.
*Margins.*—Entire.
*Texture, upper surface.*—Glabrous.

Reproductive organs:

Gynoecium:
*Pistil.*—1, with a 5-lobed stigma.
*Style length.*—2.2 cm.
*Diameter.*—0.05 cm.
*Style color.*—RHS 157C.
*Stigma color.*—RHS 145A.
*Stigma shape.*—Five lobed.
*Ovary color.*—RHS 145A.

Androecium:
*Stamens.*—5, surrounding the style and stigma.
*Filaments.*—Fused with the base of the flower.
*Anther.*—Elongated.
*Anther color.*—RHS 159A.
*Anther length.*—0.9 cm.
*Color of pollen.*—RHS 159D.
*Pollen amount.*—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0031' substantially as illustrated and described herein.

* * * * *